(12) United States Patent
Zaro et al.

(10) Patent No.: US 9,370,591 B2
(45) Date of Patent: Jun. 21, 2016

(54) SYSTEM FOR GENERATING VAPORIZED HYDROGEN PEROXIDE FOR FILLERS

(71) Applicant: Scholle Corporation, Irvine, CA (US)

(72) Inventors: Christopher Zaro, Arlington Heights, IL (US); Sean Michael Fitzgerald, West Dundee, IL (US)

(73) Assignee: Scholle IPN Corporation, Northlake, IL (US)

( * ) Notice: Subject to any disclaimer, the term of this patent is extended or adjusted under 35 U.S.C. 154(b) by 61 days.

(21) Appl. No.: 14/290,631

(22) Filed: May 29, 2014

(65) Prior Publication Data
US 2015/0343106 A1 Dec. 3, 2015

(51) Int. Cl.
*A61L 2/20* (2006.01)
*F04B 41/06* (2006.01)
*F04B 23/04* (2006.01)

(52) U.S. Cl.
CPC .................. *A61L 2/208* (2013.01); *F04B 23/04* (2013.01); *F04B 41/06* (2013.01); *Y10T 137/0419* (2015.04); *Y10T 137/4245* (2015.04)

(58) Field of Classification Search
CPC ............ E03B 5/00; F04B 23/04; F04B 23/06; F04B 41/06; F04B 41/02; A61L 2/208
USPC .................. 137/624.13, 565.29, 565.33
See application file for complete search history.

(56) References Cited

U.S. PATENT DOCUMENTS

| | | | | |
|---|---|---|---|---|
| 4,089,662 A | * | 5/1978 | Williams | B01D 3/00 196/132 |
| 8,206,134 B2 | * | 6/2012 | Moldovan | F04B 23/026 137/565.19 |
| 8,343,098 B2 | * | 1/2013 | Nystrom | A61M 5/007 604/122 |
| 2010/0272581 A1 | * | 10/2010 | Morriss | F04B 43/113 417/53 |

* cited by examiner

*Primary Examiner* — Kevin Lee
(74) *Attorney, Agent, or Firm* — The Watson I.P. Group, PLC; Jovan N. Jovanovic; Vladan M. Vasiljevic

(57) ABSTRACT

A vapor hydrogen peroxide system and method that includes a reservoir assembly, a first pump assembly, a second pump assembly, a test assembly and a heating assembly. The system is configured to operate sequentially switching between the first pump assembly and the second pump assembly. The pump assembly that is to be utilized is directed through a recirculation procedure prior to the switching, to, in turn, purge any air bubbles that may have amassed within the pump assembly prior to switching.

13 Claims, 2 Drawing Sheets

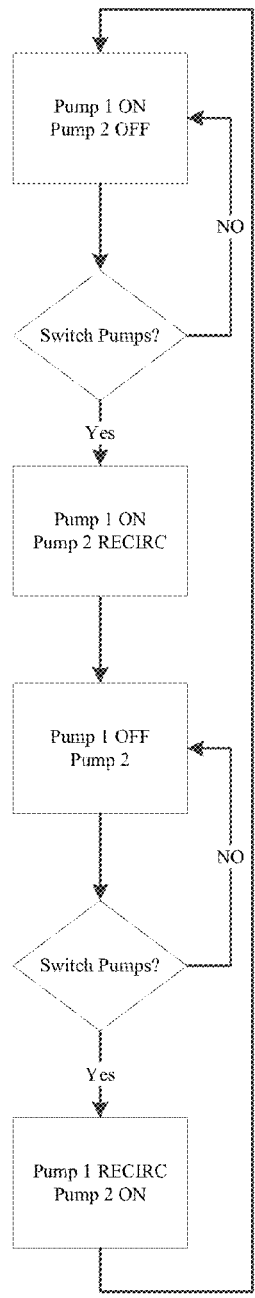
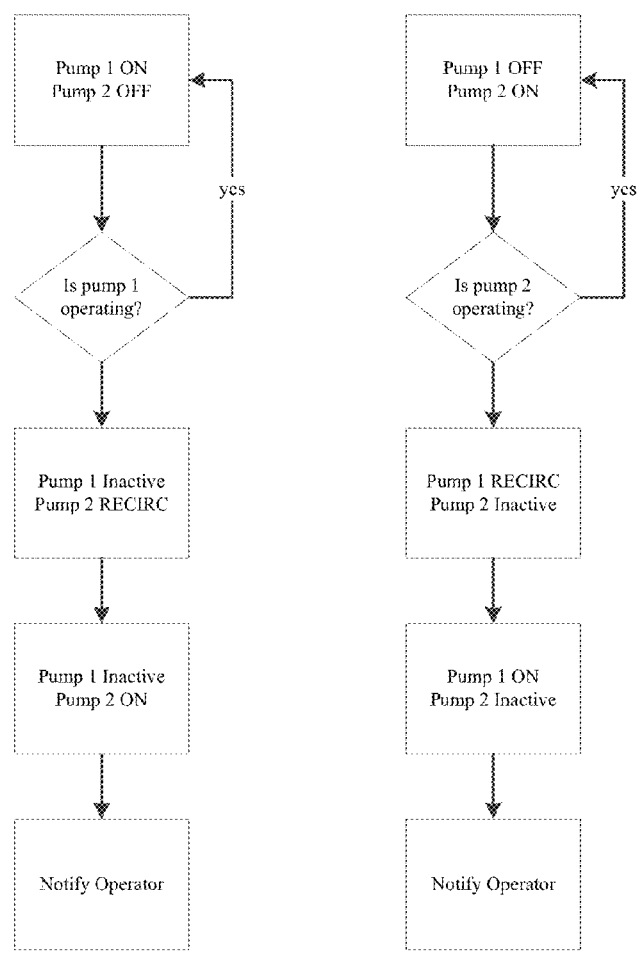
Figure 2
Figure 3
Figure 4

SYSTEM FOR GENERATING VAPORIZED HYDROGEN PEROXIDE FOR FILLERS

CROSS-REFERENCE TO RELATED APPLICATION

NA

BACKGROUND OF THE DISCLOSURE

1. Field of the Disclosure

The invention relates in general to fillers which are configured to fill packages with a flowable material, and more particularly, to systems for sanitizing the filling process, or, in other terms, a system for generating vaporized hydrogen peroxide for use in association with a filler.

2. Background Art

The use of hydrogen peroxide and vapor hydrogen peroxide for purposes of sanitizing fillers is known in the art. Problematically, prior art vapor hydrogen peroxide generator systems do not have a manner to reduce gasification of hydrogen peroxide when utilized in a continuous and/or semi-continuous production process. The gasification of hydrogen peroxide can cause the incorrect metering of flow rate measurement which lowers the effectiveness of the overall system. Gasification often occurs if a relatively large volume is permitted to stay in a container for extended periods of time, or if fluid lines are not cleared and the fluid is allowed to linger in the lines.

Additionally, and also problematically, prior art vapor hydrogen peroxide generator systems do not have a manner in which to interrupt the flow of vaporized hydrogen peroxide when filling equipment is in a standby or an idle state. An idle state is a frequent occurrence, for example, when performing a product changeover or maintenance or other interruption. Often, after an idle state, a long restart time is experienced. On the other hand, keeping the system in a running state causes excess usage of hydrogen peroxide, as well as causing unsafe exposure to vapor hydrogen peroxide.

SUMMARY OF THE DISCLOSURE

The disclosure is directed a method of operating a vapor hydrogen peroxide system comprising: providing a first pump assembly including a first transfer pump and a first injector; providing a second pump assembly including a second transfer pump and a second injector; providing a hydrogen peroxide reservoir in operable communication with each of the first and second pump assemblies; operating the first pump assembly to direct a fluid from the hydrogen peroxide reservoir to the first injector; initiating the second pump assembly to recirculate the fluid from the hydrogen peroxide reservoir through the second pump and back to the hydrogen peroxide reservoir; after a predetermined amount of time, operating the second pump assembly to direct a fluid from the hydrogen peroxide reservoir to the second injector; and stopping the operation of the first pump assembly after the step of operating the second pump assembly.

In some examples, the method further comprises the steps of: initiating the first pump assembly to recirculate the fluid from the hydrogen peroxide reservoir to through the first pump and back to the hydrogen peroxide reservoir; after a predetermined amount of time, operating the first pump assembly to direct a fluid from the hydrogen peroxide reservoir to the first injector; and stopping the operation of the first pump assembly after the step of operating the second pump assembly.

In some examples, the method further comprises the step of: refilling the reservoir when the fluid is reduced to a predetermined level; and sequentially undertaking the steps of initiating the first pump assembly and initiating the second pump assembly such that the switch between the first pump assembly and the second pump assembly occurs at each step of refilling.

In some examples, the reservoir has a capacity of less than one liter.

In some examples, the method further comprises the steps of: sensing a failure in the first pump assembly or the second pump assembly; and starting the step of initiating the first pump assembly or the second pump assembly based on the sensed failure, so as to initiate the operation of the pump assembly that has not incurred a failure.

In some examples, the method further comprises the step of: notifying an operator of the failure sensed in the first pump assembly or second pump assembly.

In another aspect of the disclosure, the disclosure is directed to a vapor hydrogen peroxide generating system comprising a hydrogen peroxide reservoir, a first pump assembly and a second pump assembly. The first pump assembly includes a first pump, a first recirculation valve and a first injector. The first pump is in communication with the first recirculation valve and the hydrogen peroxide reservoir. The first injector is in fluid communication with the first recirculation valve. The second pump assembly has a second pump, a second recirculation valve and a second injector. The second pump is in communication with the second recirculation valve and the hydrogen peroxide reservoir. The second injector is in fluid communication with the second recirculation valve. The system is structurally configured to sequentially selectively shift operating between the first pump assembly and the second pump assembly at predetermined intervals. Prior to the shift to a next pump assembly, the next pump assembly is operated in a recirculation procedure.

In some examples, the vapor hydrogen peroxide generating system further includes a bulk tank including a pump in communication with each of the bulk tank and the hydrogen peroxide reservoir. The bulk tank is larger than the hydrogen peroxide reservoir in capacity.

In some examples, a heating assembly is configured to provide heated fluid, typically air, or another fluid in gaseous form, to a vaporizer containing the first injector and the second injector, to, in turn, heat the vaporizer.

In another aspect of the disclosure, the disclosure is directed to a method of operating a vapor hydrogen peroxide system. The method comprising the steps of: providing a first pump assembly including a first transfer pump and a first injector; providing a second pump assembly including a second transfer pump and a second injector; providing a hydrogen peroxide reservoir in operable communication with each of the first and second pump assemblies; operating the first pump assembly to direct a fluid from the hydrogen peroxide reservoir to the first injector; recirculating the fluid within the second pump assembly; after a predetermined amount of time, operating the second pump assembly to direct a fluid from the hydrogen peroxide reservoir to the second injector; and stopping the operation of the first pump assembly commensurate the step of operating the second pump assembly.

In some examples, the method further comprises the steps of: recirculating the fluid within the first pump; after a predetermined amount of time, operating the first pump assembly to direct a fluid from the hydrogen peroxide reservoir to the first injector; and stopping the operation of the first pump assembly commensurate the step of operating the second pump assembly.

In some examples, the method further comprises the steps of refilling the reservoir when the fluid is reduced to a predetermined level; and sequentially undertaking the steps of initiating the first pump assembly and initiating the second pump assembly such that the switch between the first pump assembly and the second pump assembly occurs at each step of refilling.

In some examples, the reservoir has a capacity of less than one liter.

BRIEF DESCRIPTION OF THE DRAWINGS

The disclosure will now be described with reference to the drawings wherein:

FIG. 2 of the drawings is a flow chart of one operating paradigm in which the sequential change from pump to pump is shown;

FIG. 3 of the drawings is a flow chart corresponding to an operating paradigm in which the first pump assembly (pump 1) in some manner fails or becomes inactive; and FIG. 4 of the drawings is a flow chart corresponding to an operating paradigm in which the second pump assembly (pump 2) in some manner fails or becomes inactive.

DETAILED DESCRIPTION OF THE DISCLOSURE

Figure 1:
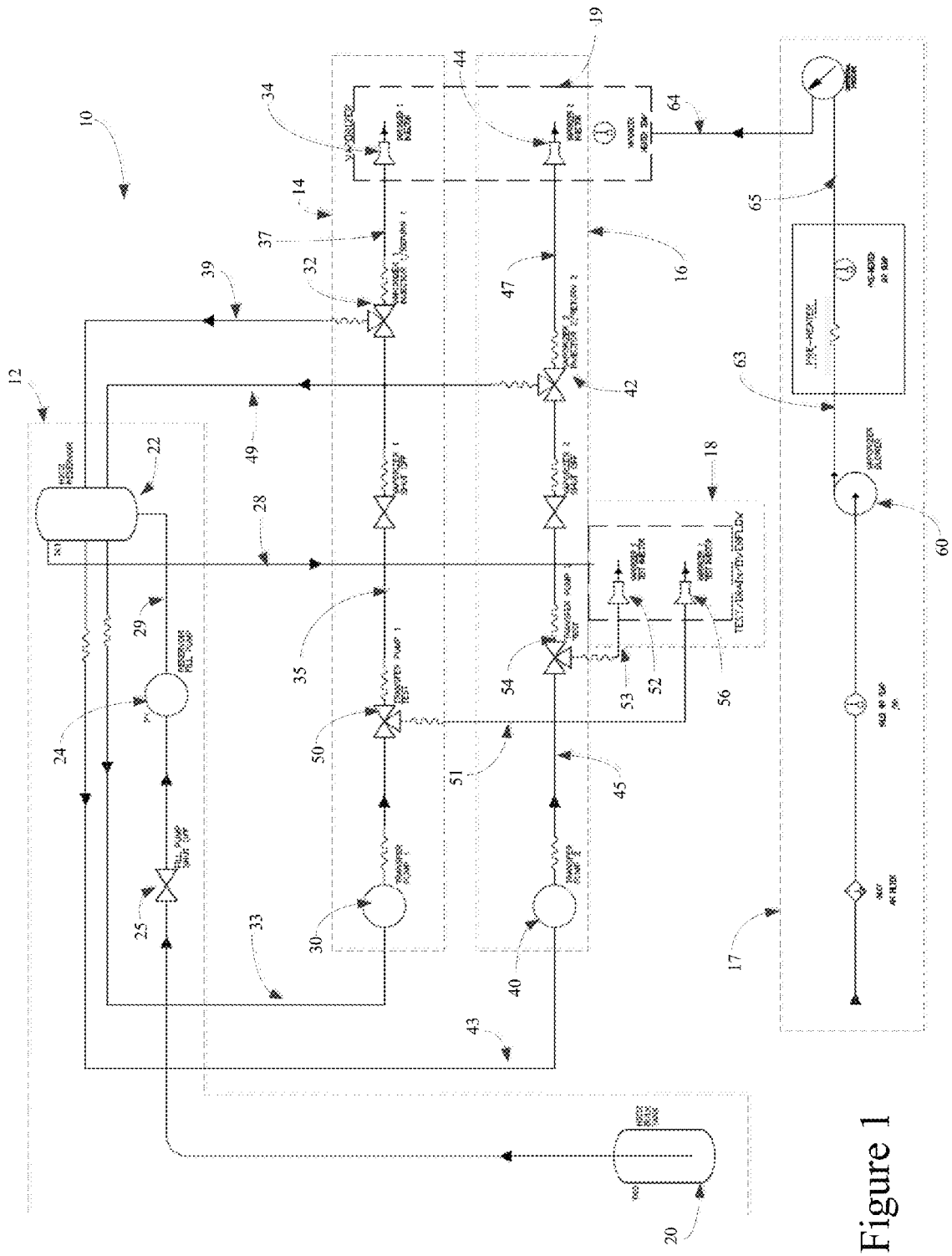
FIG. 1 of the drawings is a schematic representation of the system of the present disclosure.

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Referring now to the drawings and in particular to FIG. 1, a schematic representation of the system for generating vaporized hydrogen peroxide for fillers is shown generally at 10. The system can be incorporated into a filler which is configured to fill flexible containers (i.e., the bags of a bag in box package). Typically the flexible containers include a plurality of panels that are joined together with seals to form a fluid tight cavity. A spout is coupled to one or more of the panels to provide ingress into the fluid tight cavity. Often, a cap or cover is positioned over the spout to seal the opening.

The system 10 includes reservoir assembly 12, first pump assembly 14, second pump assembly 16, test assembly 18, heater assembly 17 and vaporizer assembly 19. Each of the assemblies 12, 14, 16 and 18 are coupled together through various fluid carrying lines (such as flexible polymer tubing or the like). The heater assembly 17 provides the heated air for the vaporizer 19.

The reservoir assembly 12 includes bulk tank 20, hydrogen peroxide reservoir 22 and pump 24. The bulk tank 20 is coupled to the hydrogen peroxide reservoir 22 by way of reservoir refill line 29. Typically, the hydrogen peroxide reservoir is on the order of one liter or smaller, while not limited thereto. For example, in the contemplated embodiment, the hydrogen peroxide reservoir is on the order of 306 ml. One reservoir that is contemplated for use in association with the present system is disclosed in U.S. patent application Ser. No. 14/190,571 filed Feb. 26, 2014, entitled "Reservoir Assembly For Storing hydrogen Peroxide For Use With A Hydrogen Peroxide Vaporizer In Association With A Filler" which is assigned to Scholle Corporation, the entire disclosure of which is hereby incorporated by reference in its entirety. Through typical operation, it is contemplated that the reservoir 22 is typically emptied within 15 minutes and more preferably in 12 minutes. While longer times are contemplated, it has been shown that with a reservoir that retains the hydrogen peroxide solution for such a period of time tends to minimize the amassing of air bubbles.

Pump 24 is positioned along the reservoir refill line and is configured to pull fluid from the bulk tank 20 and deliver the same to the hydrogen peroxide reservoir 22. It will be understood that various electronics may be incorporated to insure that the pump 24 directs the appropriate amount of fluid to the hydrogen peroxide reservoir. A overflow and drain line 28 may be coupled to the hydrogen peroxide reservoir to allow for the draining of the reservoir, and, also, to assist with fluid removal in the event that the reservoir is overfilled.

The first pump assembly 14 is shown in FIG. 1 as comprising first transfer pump 30, recirculation valve 32 and injector 34. The first transfer pump is coupled to the hydrogen peroxide reservoir 22 by way of the first pump inlet line 33. The first transfer pump is coupled to the recirculation valve by way of pump line 35. The recirculation valve 32 is coupled to the injector 34 by way of injector line 37. The recirculation valve is coupled to the hydrogen peroxide reservoir 22 by way of recirculation line 39. As will be explained, the first pump is configured to either direct hydrogen peroxide fluid from the hydrogen peroxide reservoir to the injector or to recirculate back to the reservoir. The injector 34 is located in the vaporizer 19. It will be understood that while a single injector is shown, multiple injectors may be utilized coupled to the injector line 37.

The second pump assembly 16 is shown in FIG. 1 as comprising second transfer pump 40, recirculation valve 42 and injector 44. The second transfer pump is coupled to the hydrogen peroxide reservoir 22 by way of the second pump inlet line 43. The second transfer pump is coupled to the recirculation valve by way of pump line 45. The recirculation valve 42 is coupled to the injector 44 by way of injector line 47. The recirculation valve is coupled to the hydrogen peroxide reservoir 22 by way of recirculation line 49. As will also be explained, the second pump is configured to either direct hydrogen peroxide fluid from the hydrogen peroxide reservoir to the injector or to recirculate back to the reservoir. The injector 44 is located in the vaporizer 19. It will be understood that while a single injector is shown, multiple injectors may be utilized coupled to the injector line 47.

The test assembly 18 is shown in FIG. 1 as comprising first pump valve 50, first pump test injector 52, as well as second pump valve 54 and second pump test injector 56. The first pump valve 50 is coupled to the pump line 35 and provides a manner by which to draw fluid that is within that line to the test injector 52 along test line 51. Similarly, the second pump valve 54 is coupled to the pump line 45 and provides a manner by which to draw fluid that is within that line to the test injector 56 along test line 53. Generally, such a testing system is utilized and activated to test the operation of the pumps and the movement of hydrogen peroxide fluid from the reservoir. In other embodiments the test injectors may be replaced with fittings, or other terminating or dispensing members.

The heater assembly 17 includes blower 60 and heater 62. The blower 60 is coupled to the heater 62 through heat line 63. The heater is coupled to the vaporizer 19 through vaporizer line 65. The heater assembly provides heated gaseous fluids, such as air to the vaporizer 19.

In operation, tank 20 is filled with a large quantity of hydrogen peroxide. From the tank 20, it is necessary to fill the hydrogen peroxide reservoir 22. This is achieved through the use of pump 24 which directs a quantity of fluid from the tank 20 to the reservoir 22. It will be understood that the reservoir is generally of a smaller size as described above so as to retain a smaller quantity of hydrogen peroxide such that frequent refilling is necessary. By keeping the tank rather small, the creation of off gasses from the hydrogen peroxide solution can be minimized as the reservoir is being emptied and refilled at a relatively high rate.

With reference to FIG. 2, in the normal course of operation, the system is configured to sequentially utilize the first pump assembly 14 and the second pump assembly 16, such that after a predetermined period of time, they alternate in use. In one example, the pump assemblies can be used in alternating fashion, switching from one to the other each time the reservoir is refilled. Such a dual pump assembly provides for reduced maintenance time, as well as redundancy in the event of a malfunction.

In the situation wherein the first pump assembly 14 is being utilized, the pump is activated drawing fluid from reservoir 22 through first pump inlet line 33. The fluid is then directed through the pump line 35 through the recirculation valve 32 and to the injector 34 through injector line 37. The recirculation valve 32 is set to allow fluid to pass to injector line 37 while precluding passage of fluid through recirculation line 39.

At the same time, the second pump assembly 16 is off and the pump is not operating. In many instances, there is fluid in the second pump inlet line 43 and pump line 45 that has remained after the second pump assembly 16 was last utilized. From prolonged sitting, the fluid may amass larger air bubbles that are disruptive to the operation of the injector.

The system continues in this manner until it is desired to switch from the first pump assembly 14 to the second pump assembly 16. In such an instance, at a point prior to switching, the second pump assembly 16 is activated in a recirculation mode. That is, the pump 40 is activated and fluid is directed from the reservoir 22 through the second pump inlet line 43. The fluid is pumped through the pump line 45 to the recirculation valve. The recirculation valve is actuated in such a manner that precludes passage of fluid to the injector line 47 while allowing the passage of fluid to the recirculation line 49. Thus, as the pump remains activated, the fluid is being recirculated through the recirculation line 49 back to the reservoir. This step purges the liens 43 and 45 from any air bubbles that have accumulated due to the stationary fluid.

Once enough fluid has been sent through the second pump assembly to essentially purge the lines, the recirculation valve 42 is reoriented to preclude passage of fluid to the recirculation line 49 and to direct fluid to the injector line 47 for delivery to the injector 44. At the same time, the first pump assembly is turned off such that the fluid is no longer being pumped through the lines 33, 35 or 37. More precisely, the first pump assembly can be turned off commensurate with the second pump beginning, which may be at the same time as the second pump starts, a small period of time before the second pump starts, or after the second pump has started. That is, the timing of the cessation of the first pump is at or near the starting of the second pump as it is not necessary to run both of the injectors simultaneously.

Eventually, it becomes desirable to again switch back to the first pump assembly. Steps analogous to that which was described above are undertaken. In particular, the first pump assembly is put into a recirculation mode prior to switching back to the first pump assembly. More particularly, the first pump 30 is activated which draws fluid from the reservoir through the first pump inlet line 33. The fluid is directed to recirculation valve 32 through the pump line 35. The recirculation valve is configured to direct the fluid through recirculation line 39 back to the reservoir 22. This continues until the line has been purged of any air bubbles that may have amassed while the first pump assembly was in the off position.

Once the first pump assembly has been run for a predetermined period of time, the switch is made to recirculation valve so that the fluid is directed to the injector 34 through injector line 37 and not the recirculation line 39. At the same time, the second pump assembly 16 is turned off. During this switch over from the second pump to the first pump, the reservoir 22 can be replenished by the reservoir assembly directing fluid from the bulk tank 20 by way of pump 24. As stated above, the switch between pump assemblies can occur before or after or during each refilling of the reservoir, or can otherwise be timed to the refilling of the reservoir.

Such a process may continue as long as desired. In instances wherein it is necessary to maintain either one of the pumps in a ready mode, it is contemplated that after a predetermined period of time, a recirculation procedure is undertaken to remove the air bubbles from the lines. In particular, the first pump assembly 14 or the second pump assembly 16 are activated in a recirculation procedure to purge the lines. As a result, the system is ready to operate from either pump assembly, as necessary.

In the event of a fault with one of the pump assemblies, the other pump assembly can be configured to take over on a very short notice. For example, and with reference to FIG. 3, in the event of a failure to the first pump assembly during operation, the first pump assembly can be deactivated or stopped. Next, the second pump assembly is activated in a recirculation procedure that purges the line of any air bubbles. Once purged, the recirculation valve can be configured to direct fluid to the second injector 44. At the same time, the system can notify the operator that a fault has occurred with the first pump. Additionally, the system can be configured to turn off after the reservoir is emptied, or may be configured to go into a standby mode, or may be configured to continue operating with a single pump for a plurality of cycles. A similar procedure occurs with respect to a failure of the second pump assembly. Such a procedure is shown in FIG. 4.

From time to time it may become necessary to test the operation of either the first or second pump assembly. In the case of the testing of the first pump assembly, the user can first activate the first pump valve 50 to direct fluid to the test line 51 instead of the pump line 35. Next, the first pump 30 is activated and fluid is delivered from the reservoir 22 through the first pump inlet line 33 to the first pump valve 50 and then through the test line 51 to the first pump test injector 52. Similarly, in the case of the second pump assembly, the user can first activate the second pump valve 54 to direct fluid to the test line 53 instead of pump line 45. Next, the second pump 40 is activated and fluid is delivered from the reservoir 22 through the second pump inlet line 43 to the second pump valve 54. Next, the fluid is delivered through the test line 53 to the second pump test injector 56. These may be tested separately (that is, in sequence), or may be tested simultaneously.

It is contemplated that an additional pump assembly may be provided, such that each one of the pump assemblies operates sequentially. It will be understood that the additional pump would provide further redundancy and would provide further operation in the event that one of the pump assemblies was compromised.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A method of operating a vapor hydrogen peroxide system comprising:
   providing a first pump assembly including a first transfer pump and a first injector;
   providing a second pump assembly including a second transfer pump and a second injector;
   providing a hydrogen peroxide reservoir in operable communication with each of the first and second pump assemblies;
   operating the first pump assembly to direct a fluid from the hydrogen peroxide reservoir to the first injector;
   initiating the second pump assembly to recirculate the fluid from the hydrogen peroxide reservoir through the second pump and back to the hydrogen peroxide reservoir;
   after a predetermined amount of time, operating the second pump assembly to direct a fluid from the hydrogen peroxide reservoir to the second injector; and
   stopping the operation of the first pump assembly after the step of operating the second pump assembly.

2. The method of claim 1 further comprising the steps of:
   initiating the first pump assembly to recirculate the fluid from the hydrogen peroxide reservoir to through the first pump and back to the hydrogen peroxide reservoir;
   after a predetermined amount of time, operating the first pump assembly to direct a fluid from the hydrogen peroxide reservoir to the first injector; and
   stopping the operation of the first pump assembly after the step of operating the second pump assembly.

3. The method of claim 2 further comprising the step of:
   refilling the reservoir when the fluid is reduced to a predetermined level; and
   sequentially undertaking the steps of initiating the first pump assembly and initiating the second pump assembly such that the switch between the first pump assembly and the second pump assembly occurs at each step of refilling.

4. The method of claim 3 wherein the reservoir has a capacity of less than one liter.

5. The method of claim 1 further comprising the steps of:
   sensing a failure in the first pump assembly or the second pump assembly; and
   starting the step of initiating the first pump assembly or the second pump assembly based on the sensed failure, so as to initiate the operation of the pump assembly that has not incurred a failure.

6. The method of claim 5 further comprising the step of:
   notifying an operator of the failure sensed in the first pump assembly or second pump assembly.

7. A vapor hydrogen peroxide generating system comprising:
   a hydrogen peroxide reservoir;
   a first pump assembly having a first pump, a first recirculation valve and a first injector, the first pump in communication with the first recirculation valve and the hydrogen peroxide reservoir, and the first injector in fluid communication with the first recirculation valve;
   a second pump assembly having a second pump, a second recirculation valve and a second injector, the second pump in communication with the second recirculation valve and the hydrogen peroxide reservoir, and the second injector in fluid communication with the second recirculation valve; and
   the system structurally configured to sequentially selectively shift operating between the first pump assembly and the second pump assembly at predetermined intervals, wherein prior to the shift to a next pump assembly, the next pump assembly is operated in a recirculation procedure.

8. The vapor hydrogen peroxide generating system of claim 7 further comprising a bulk tank including a pump in communication with the bulk tank and the hydrogen peroxide reservoir, the bulk tank being larger than the hydrogen peroxide reservoir in capacity.

9. The vapor hydrogen peroxide generating system of claim 7 further comprising a heating assembly configured to provide heated fluid, to a vaporizer containing the first injector and the second injector, to, in turn, heat the vaporizer.

10. A method of operating a vapor hydrogen peroxide system comprising:
    providing a first pump assembly including a first transfer pump and a first injector;
    providing a second pump assembly including a second transfer pump and a second injector;
    providing a hydrogen peroxide reservoir in operable communication with each of the first and second pump assemblies;
    operating the first pump assembly to direct a fluid from the hydrogen peroxide reservoir to the first injector;
    recirculating the fluid within the second pump assembly;
    after a predetermined amount of time, operating the second pump assembly to direct a fluid from the hydrogen peroxide reservoir to the second injector; and
    stopping the operation of the first pump assembly commensurate the step of operating the second pump assembly.

11. The method of claim 10 further comprising the steps of:
    recirculating the fluid within the first pump;
    after a predetermined amount of time, operating the first pump assembly to direct a fluid from the hydrogen peroxide reservoir to the first injector; and
    stopping the operation of the first pump assembly commensurate the step of operating the second pump assembly.

12. The method of claim 11 further comprising the step of:
    refilling the reservoir when the fluid is reduced to a predetermined level; and
    sequentially undertaking the steps of operating the first pump assembly and operating the second pump assembly such that a switch between the first pump assembly and the second pump assembly occurs at each step of refilling.

13. The method of claim 12 wherein the reservoir has a capacity of less than one liter.

* * * * *